(12) United States Patent
Salah et al.

(10) Patent No.: US 10,588,501 B2
(45) Date of Patent: Mar. 17, 2020

(54) DENTAL IMAGING DEVICE

(71) Applicant: DENTAL MONITORING, Paris (FR)

(72) Inventors: Philippe Salah, Bagnolet (FR);
Laurent Debraux, Paris (FR);
Guillaume Ghyselinck, Cantin (FR);
Thomas Pellissard, Clichy (FR)

(73) Assignee: DENTAL MONITORING, Paris (FR)

( * ) Notice: Subject to any disclaimer, the term of this patent is extended or adjusted under 35 U.S.C. 154(b) by 0 days.

(21) Appl. No.: 15/953,561

(22) Filed: Apr. 16, 2018

(65) Prior Publication Data

US 2018/0303331 A1 Oct. 25, 2018

(30) Foreign Application Priority Data

Apr. 19, 2017 (FR) ...................................... 17 53389

(51) Int. Cl.
*A61B 1/247* (2006.01)
*H04N 5/225* (2006.01)
*H04M 1/02* (2006.01)
*A61B 1/06* (2006.01)
*A61B 1/045* (2006.01)
(Continued)

(52) U.S. Cl.
CPC .......... *A61B 1/247* (2013.01); *A61B 1/00057* (2013.01); *A61B 1/00105* (2013.01); *A61B 1/00181* (2013.01); *A61B 1/045* (2013.01); *A61B 1/0669* (2013.01); *A61B 1/32* (2013.01); *A61B 5/0079* (2013.01); *A61B 5/0088* (2013.01); *A61B 5/1032* (2013.01); *A61C 5/90* (2017.02); *A61C 9/0053* (2013.01); *H04M 1/0202* (2013.01); *H04N 5/2257* (2013.01); *A61B 1/042* (2013.01); *A61B 5/742* (2013.01); (Continued)

(58) Field of Classification Search
CPC ........... A61B 1/247; A61B 1/24; A61B 5/742; A61B 5/0088; A61C 9/0053
See application file for complete search history.

(56) References Cited

U.S. PATENT DOCUMENTS

2004/0064019 A1 4/2004 Chang et al.
2006/0040230 A1 2/2006 Blanding et al.
(Continued)

FOREIGN PATENT DOCUMENTS

DE 102009017819 A1 10/2010
EP 0420715 A1 4/1991
(Continued)

OTHER PUBLICATIONS

Corresponding French Application, French Search Report, Application No. 1753389, dated Jan. 3, 2018, 2 pages.
(Continued)

*Primary Examiner* — Nam D Pham
(74) *Attorney, Agent, or Firm* — Cooper Legal Group, LLC; Ronald M. Kachmarik

(57) ABSTRACT

An imaging device including a support, a dental retractor fastened to the support and defining a retractor opening, a mirror fastened to at least one of the support and the retractor, and structure for fastening an image acquisition apparatus to the support in a position in which the acquisition apparatus is oriented so as to receive a composite image including a direct image of the retractor opening and an image of the retractor opening reflected by the mirror.

19 Claims, 4 Drawing Sheets

(51) Int. Cl.
*A61B 1/32* (2006.01)
*A61C 5/90* (2017.01)
*A61C 9/00* (2006.01)
*A61B 5/00* (2006.01)
*A61B 5/103* (2006.01)
*A61B 1/00* (2006.01)
*A61B 1/04* (2006.01)
*A61C 7/00* (2006.01)

(52) U.S. Cl.
CPC ....... *A61B 2560/0228* (2013.01); *A61C 7/002* (2013.01); *H04N 2005/2255* (2013.01)

(56) References Cited

U.S. PATENT DOCUMENTS

| | | | |
|---|---|---|---|
| 2014/0005484 A1* | 1/2014 | Charles | A61B 17/02 600/201 |
| 2015/0234192 A1 | 8/2015 | Lyons | |
| 2018/0000563 A1 | 1/2018 | Shanjani et al. | |
| 2018/0228359 A1* | 8/2018 | Meyer | A61B 1/24 |

FOREIGN PATENT DOCUMENTS

| | | |
|---|---|---|
| EP | 1252858 A2 | 10/2002 |
| FR | 3004098 A1 | 10/2014 |
| FR | 3027506 A1 | 4/2016 |
| JP | 2005168520 A | 6/2005 |
| WO | 2016066651 A1 | 5/2016 |

OTHER PUBLICATIONS

I. Ahmad: "Digital dental photography Part 8: intra-oral set-ups" BDJ, vol. 207, No. 4, Aug. 22, 2009 (Aug. 22, 2009), pp. 151-157, XP055209322, ISSN: 0007-0610, DOI:10.1038/sj.bdj.2009.715; Entire Document.
U.S. Appl. No. 15/952,635.
U.S. Appl. No. 15/953,561.
U.S. Appl. No. 15/953,744.
U.S. Appl. No. 15/990,950.
U.S. Appl. No. 16/001,049.
U.S. Appl. No. 16/030,032.
U.S. Appl. No. 16/030,137.
U.S. Appl. No. 16/031,125.
U.S. Appl. No. 16/031,172.
U.S. Appl. No. 16/031,201.

* cited by examiner

DENTAL IMAGING DEVICE

TECHNICAL FIELD

The present invention relates to a dental imaging device, in particular for implementing a method such as described in international application PCT/EP2015/074896.

PRIOR ART

PCT/EP2015/074896 describes a method allowing, on the basis of
- a three-dimensional model of the teeth of a patient produced before treatment, referred to as the "initial reference model"; then
- a simple "updated" image of the teeth taken during treatment, for example a photograph taken by the patient, the positioning of the teeth at the moment of acquisition of the updated image to be accurately evaluated.

This method consists in an iterative process in which, upon each iteration, models of teeth from the initial reference model are moved, then optimum conditions for observing the initial model thus modified (referred to as the "test reference model") are determined, the optimum observation conditions being defined as the conditions allowing the test reference model to be observed so that the view of said model is as close as possible to the updated image. A succession of "test reference models" are tested until obtaining a maximum level of correspondence between a test reference model and the updated image. This last test reference model is then considered to be representative of the teeth in their position at the moment of acquisition of the updated image. Ideally, this model, referred to as the "updated reference model", is a digital three-dimensional reference model from which the updated image could have been taken had this model been real. In practice, it actually represents, with a high level of accuracy, the teeth in their position at the moment of acquisition of the updated image.

Generally, multiple updated images are required to evaluate the positioning of multiple teeth. The method must be implemented for each updated image. The method described in international application PCT/EP2015/074896 may therefore be lengthy in its implementation.

Furthermore, the updated images may be used to detect variations in the appearance of the teeth or of the soft tissues such as the gums, and in particular in their color and in their translucence. Comparing various photos does not however always yield satisfactory results.

One object of the present invention is to provide an at least partial response to these problems.

SUMMARY OF THE INVENTION

The invention provides an imaging device including:
a support;
a dental retractor fastened to the support and defining a retractor opening;
means for fastening an image acquisition apparatus to the support in a position in which the acquisition apparatus is oriented so as to receive an image of the retractor opening.

According to a first main aspect, the device includes a mirror fastened to the support and/or to the retractor, and the fastening means are configured to fasten the image acquisition apparatus to the support in a position in which the acquisition apparatus is oriented so as to receive a composite image including a direct image of the retractor opening and an image of the retractor opening reflected by the mirror.

In a service position in which the retractor is positioned on the mouth of the patient and the image acquisition apparatus is fastened to the support by said fastening means, said acquisition apparatus thus sees a composite image including a direct image of the teeth that is observed directly through the retractor opening and a reflected image of the teeth returned by the mirror.

As will become more clearly apparent later on in the description, a device according to the first main aspect of the invention thus allows multiple images of the teeth, observed from different angles, to be acquired simultaneously. The acquisition process is accelerated as a result.

In addition, determining the conditions for acquiring the direct image, or the reflected image, makes it possible to determine the conditions for acquiring the reflected image, or the direct image, respectively. It is in fact sufficient to have knowledge of the orientation of the mirror and its position with respect to the retractor and to the acquisition apparatus in order to determine the positioning in space of the acquisition apparatus which would have allowed, in the absence of the mirror, the reflected image to be observed. The implementation of a method such as that in international application PCT/EP2015/074896 is consequently considerably accelerated as a result.

Specifically, typically, the patient takes a photo of his or her teeth from the right, a photo of his or her teeth from the left and a photo of his or her teeth from the front. However, the software implementing the method described in international application PCT/EP2015/074896 ignores the position of the acquisition apparatus in these various steps and is not able to deduce it by processing the other images. It must therefore find it again each time in order to define the optimum observation conditions.

According to a second main aspect, the device includes
a colorimetric calibration chart and/or a translucence calibration chart, preferably both a colorimetric calibration chart and a translucence calibration chart, preferably fastened to the support; and
a light source that is oriented so as to illuminate both the teeth of the patient through the retractor opening and said colorimetric calibration chart and/or said translucence calibration chart, said fastening means of the acquisition apparatus being configured to immobilize the acquisition apparatus in a position in which it is oriented so as to receive an image of both the retractor opening and of said colorimetric calibration chart and/or of said translucence calibration chart.

As will become more clearly apparent later on in the description, a device according to the second main aspect of the invention thus allows the color and the translucence of the teeth and/or of the soft tissues, such as the gums, to be accurately determined. In particular, the illumination may be monitored so as to limit disruptions due to the lighting environment of the device. Various images taken at different times may therefore be accurately compared.

Of course, the features of the two main aspects of the invention may be combined.

Regardless of the main aspect under consideration, a device according to the invention preferably has one or more of the following optional features:
the support defines a chamber that is in communication with the outside via the retractor opening and via an acquisition opening through which the acquisition apparatus fastened by said fastening means receives said composite image;

the support is telescopic so that the distance between the retractor opening and acquisition opening is variable;

the device includes at least two of said mirrors that are oriented perpendicularly to one another and each returning a reflected image of the retractor opening, each of said reflected images being represented in said composite image;

the mirror is fastened so as to extend, at least partially, preferably completely, inside the mouth of the patient in a service position in which the retractor is on the mouth of the patient;

the mirror is curved, and preferably presents a convex reflecting surface, preferably a substantially spherical reflecting surface;

the mirror is fastened to the support and/or to the retractor with an arm having a variable geometry;

the orientation of the mirror relative to the support and/or the retractor can be modified;

the image of the retractor opening which is reflected by the mirror represents the retractor opening as viewed from the side of the image acquisition apparatus, i.e. from the exterior of the mouth, or as seen from the opposite side, i.e. from the inside of the mouth;

the means for fastening the acquisition apparatus to the support can be deactivated;

the means for fastening the acquisition apparatus and/or the retractor to the support are chosen from the group consisting of a clip fastener, a self-gripping strip, clamping jaws, a screw, a magnet, a cover and a complimentary shape between the support and the acquisition apparatus;

the device includes means for fastening the retractor to the support, which means can be deactivated, the retractor thus being able to be removably fastened to the support;

the retractor includes tabs which, in a position in which the retractor is mounted on the support, are inserted into respective profiled compartments of the support, each compartment having a generally U-shaped cross section, the opening of the U preferably facing upward or downward in a service position in which the retractor is positioned on the mouth of a patient holding his or her head vertically;

in said mounted position, the retractor is kept flexed, bearing elastically on the support;

the support includes one or more, preferably two, hooks configured to accommodate the retractor in said mounted position;

the light source is configured so as to project a reference frame toward the retractor opening;

the device includes a monitoring module configured to monitor the properties of the radiation emitted by the light source, preferably as a function of the luminous radiation received by the retractor opening;

the monitoring module is configured to control the light source so that more than 50%, more than 70%, more than 90%, or even substantially 100% of the intensity of the radiation received by the retractor opening comes from the light source;

the support takes the form of a box that is in communication with the outside substantially only via the retractor opening and via an acquisition opening through which the acquisition apparatus fastened to the support receives at least one image of the retractor opening;

the device includes a processing module in which the color and translucence properties of the colorimetric and translucence calibration charts are recorded, respectively, the processing module comprising program code instructions for correcting an image representing said calibration charts so that the representations of said calibration charts on the image have said color and translucence properties.

The invention also relates to:

a computer program, and in particular a specialized mobile phone app, comprising program code instructions for
  guiding an operator during an adjustment to the geometry of the support and/or when orienting the mirror and/or when positioning the mouth of the patient on the retractor, and/or
  controlling one or more actuators that are capable of modifying said geometry, in particular modifying the length of the support, and/or said orientation of the mirror;

a computer medium on which such a program is recorded, for example a memory or a CD-ROM; and a personal device, in particular mobile phone or a tablet, on which such a program is loaded.

The invention also relates to an imaging kit including:

an imaging device according to the invention; and an image acquisition apparatus, preferably fastened to the device so as to acquire said images, and in particular said composite image.

A kit according to the invention preferably has one or more of the following optional features:

the acquisition apparatus is a mobile phone;

the image acquisition apparatus includes a computer program according to the invention;

the image acquisition apparatus is configured to take multiple photographs in succession, with different focal lengths, as a result of a single trigger action.

Definitions

A "patient" is understood to mean any person for whom a device according to the invention may be implemented, whether this person is sick or not, or whether this person is currently being treated or not. A device according to the invention may be used for an animal other than a human being.

A "mobile phone" is a device weighing less than 500 g, provided with a sensor enabling it to capture images, capable of exchanging data with another device more than 500 km away from the mobile phone, and capable of displaying said data, and in particular said images.

The "acquisition conditions" for acquiring an image of the teeth specify the position and the orientation in space of an image acquisition apparatus in relation to the teeth of the patient, and preferably the calibration of this image acquisition apparatus, in order to acquire, at the time of said acquisition, by direct observation, said image. The acquisition conditions for acquiring a reflected image therefore specify the position and orientation in space that the image acquisition apparatus would have had to have taken, in the absence of the mirror, in order to acquire the reflected image.

The "calibration" of an acquisition apparatus consists of the set of values of the calibration parameters. A "calibration parameter" is a parameter intrinsic to the acquisition apparatus (unlike its position and its orientation), the value of which influences the image acquired. For example, the aperture is a calibration parameter that modifies the depth of field. The exposure time is a calibration parameter that modifies the luminosity (or the "exposure") of the image. The focal length is a calibration parameter that modifies the viewing angle. i.e. the degree of "zoom". The "sensitivity"

is a calibration parameter that modifies the reaction of the sensor of a digital acquisition apparatus to incident light.

Preferably, the calibration parameters are chosen from the group formed by the aperture, the exposure time, the focal length and the sensitivity.

What is meant by an "image" is a two-dimensional image such as a photograph. An image is made up of pixels.

The term "fasten" means "fix rigidly or so as to allow only guided movement". The term "fasten" does not necessarily mean "fix definitively".

The terms "comprise", "include" and "have" should be interpreted broadly and without limitation, unless specified otherwise.

BRIEF DESCRIPTION OF THE FIGURES

Additional features and advantages of the invention will become further apparent upon reading the following detailed description and from studying the attached drawing, in which:

FIGS. 5a and 5b show different embodiments of the device of FIG. 2.

In the various figures, identical or analogous members have been denoted by the same references.

DETAILED DESCRIPTION

Device

Figure 1:
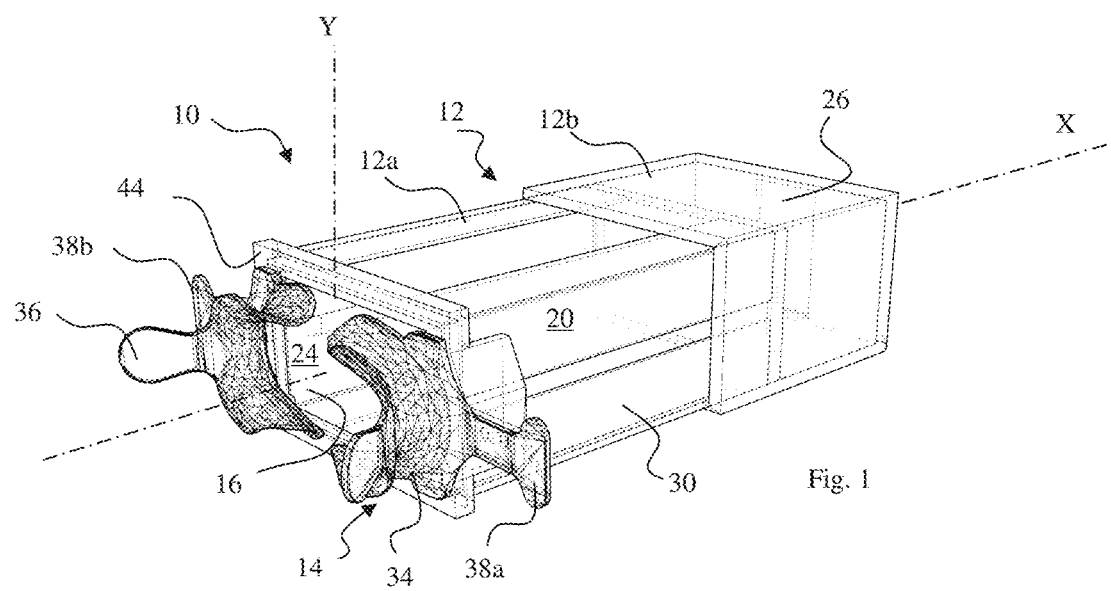
FIG. 1 shows, in perspective, an example of a device according to the invention, seen through the side of the retractor.
Figure 2:
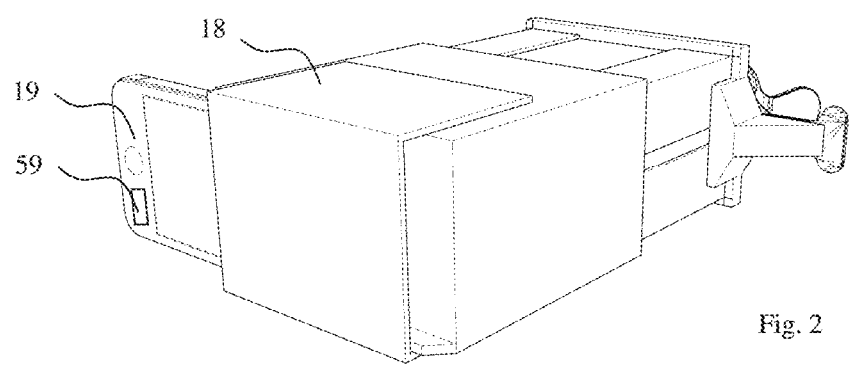
FIG. 2 shows, in perspective, an example of a device according to the invention shown from the acquisition opening side.

The imaging device 10 shown in FIG. 1 includes a support 12, taking the form of a, preferably telescopic, box, a dental retractor 14, at least one mirror 16 and fastening means 18 of an image acquisition apparatus 19, shown in FIG. 2.

Figure 5A:
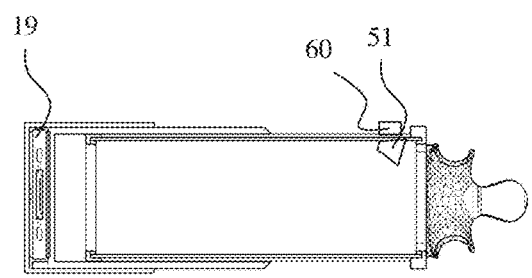
FIGS. 5a and 5b show the device of FIG. 2 with the support in retracted and deployed positions, respectively.
Figure 5B:
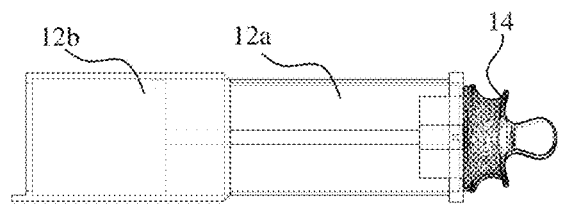

The support 12 includes a male portion 12a and a female portion 12b that are mounted so as to slide one inside the other, along a retractor axis X, between retracted (FIG. 5a) and deployed (FIG. 5b) positions. The support 12 defines a chamber 20, the length of which along the X axis depends on the relative position of the male and female portions of the support 12.

In the embodiment shown, the chamber 20 is in communication with the outside at two opposite end faces of the support 12, via a retractor opening 24 and an acquisition opening 26, respectively. The lateral wall 30 of the support 12, which extends between the two end faces, is substantially cylindrical along the X axis, and rectangular in cross section.

The box thus composed may for example be made of plastic or of cardboard.

The fastening means 18 are configured so that the image acquisition apparatus may be fastened in an acquisition position in which its objective faces the acquisition opening 26, or else obturates the acquisition opening 26.

The means 18 for fastening the acquisition apparatus to the support 12 may be of any type.

Preferably, they allow rigid fastening. Preferably, they can be deactivated, i.e. the user may dissociate the acquisition apparatus from the support whenever desired.

Preferably, the fastening means of the acquisition apparatus are chosen from the group consisting of clip-fastening means, self-gripping strips of Velcro® type, clamping jaws, screws, magnets, and complementarity of shape between the support and the acquisition apparatus. In the embodiment shown in FIG. 2, the fastening means 18 consist of a cover that may be clamped against the support 12.

In one embodiment, the fastening means 18 are suitable for fastening a conventional camera, for example of reflex type.

The retractor 14 may have the features of conventional retractors. It conventionally includes a rim 34 extending around the retractor opening 24 and arranged in such a way that the patient's lips may rest on it, leaving the patient's teeth visible through said retractor opening. In the embodiment shown, the retractor 14 also includes lobes 36 that are arranged so as to spread the cheeks away from the teeth and right 38a and left 38b tabs, which are substantially perpendicular to the X axis, facilitating the handling thereof.

The rim 34 has the shape of a channel configured to hold the patient's lips.

The retractor 14 is preferably made of a biocompatible material, for example of a plastic material.

The retractor 14 may be formed as an integral part of the support 12 or be fastened, preferably rigidly, to the support 12 by any means.

Preferably, the retractor is removable, i.e. it may be mounted on and dismounted from the support by the operator. Advantageously, the same support may therefore be used for multiple retractors, and in particular for multiple retractors of different sizes.

The means for fastening the retractor to the support may be for example clip-fastening means, self-gripping strips of Velcro® type, clamping jaws, screws, magnets, and complementarity of shape between the support and the retractor.

In one embodiment, the retractor 14 is fastened by means of insertion of one of the right 38a and left 38b tabs into a compartment of the support, then clipping the other tab onto the support.

In one embodiment, the retractor 14 is fastened by means of clipping the tabs into respective compartments of the support.

Figure 6A:
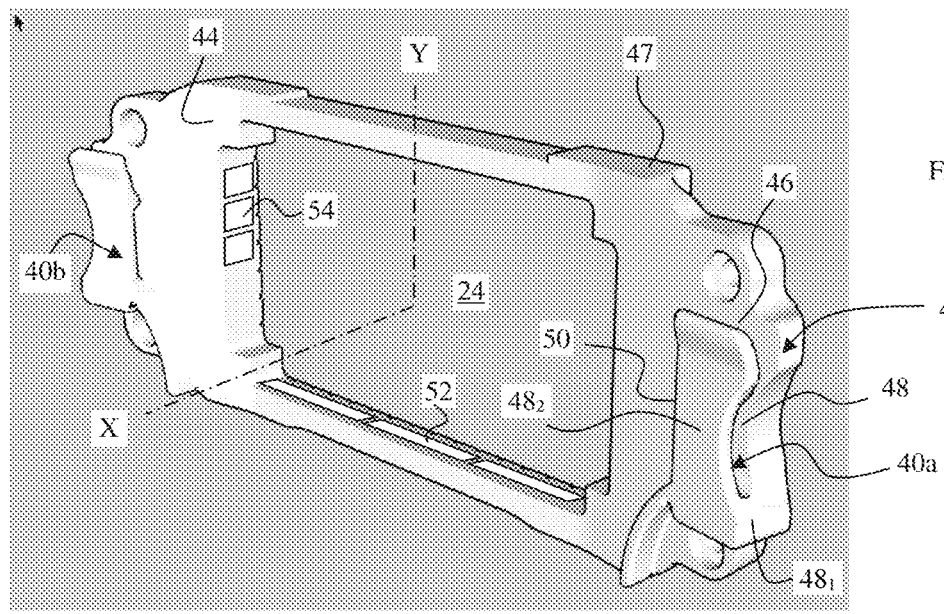
FIGS. 6a, 6b and 6c show, in perspective (FIGS. 6a and 6b) and from above (FIG. 6c), the portion of the support of a device according to the invention on which a retractor may be mounted, as shown in FIG. 6b.
Figure 6B:
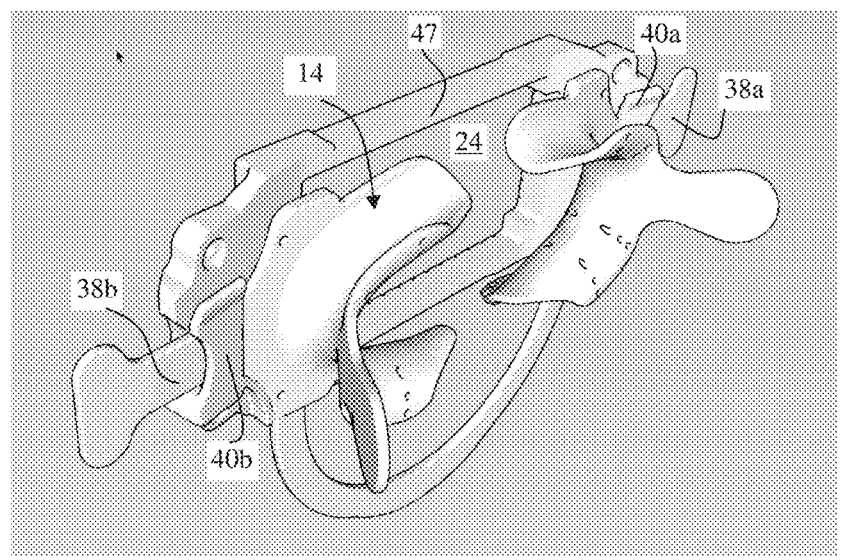

In one preferred embodiment, illustrated by FIG. 6, the means for fastening the retractor to the support include a hook onto which the retractor 14 may be hooked. The means for fastening the retractor to the support preferably include a right hook 40a and a left hook 40b that are arranged so as to accommodate the right 38a and left 38b transverse tabs of the retractor, respectively. Since the right and left hooks are similar, only one hook is described in detail below.

Preferably, said hook protrudes from the rear face 44 of the support, substantially perpendicularly to the X axis, as shown in FIG. 1. The rear face 44 is preferably defined by a plate 47 (FIG. 6a) that is fastened to an edge of the lateral wall 30 of the support 12.

Preferably, the hook takes the form of an angle 45. The angle preferably includes first and second wings that are perpendicular to one another. The first wing $48_1$, fastened to the rear face 44 of the support, is preferably substantially parallel to the X axis and the second wing $48_2$ is preferably substantially perpendicular to the X axis and, preferably, extends upward from the first wing. Along with the rear face 44 of the support, the angle 45 defines a compartment with a U-shaped profile, the main, upward-oriented opening 46 of which is sized so as to accommodate a tab of the retractor. Again preferably, the profiled compartment is open at its two right and left ends via right 48 and left 50 openings through which a tab of the retractor may be slid into the hook, i.e. between the rear face 44 of the support and the second wing $48_2$ of the angle 45, until abutting against the first wing $48_1$.

Preferably, the hooks are configured so that the retractor may be inserted therein only by force, preferably by elastically opening the hooks.

Preferably, the hooks are configured so that the retractor may be inserted therein without being deformed, preferably by flexing around an axis Y that is substantially perpendicular to the X axis, preferably substantially vertical in the service position.

Again preferably, in the position in which the retractor is mounted on the support, fastening means hold the retractor flexed around the Y axis.

Figure 6C:
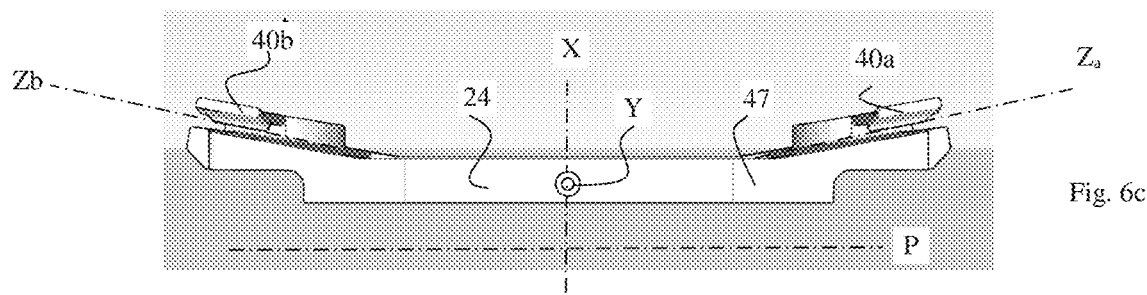

In the embodiment of FIG. 6 (FIG. 6c), the axes $Z_a$ and $Z_b$ of the angles of the left and right hooks are thus inclined with respect to a transverse plane P that is perpendicular to the X axis, while the right and left tabs of the retractor are substantially coplanar when the retractor is at rest, dissociated from the support. The width of the main openings 46 of the right and left hooks is substantially identical to the thickness of the right and left tabs of the retractor, respectively, which obliges the operator to flex the retractor around the Y axis in order to insert these tabs into these hooks. The shape of the hooks then prevents the retractor from returning to its rest position.

The elastic bearing of the retractor on the support thus obtained advantageously favors its being held in position.

In one embodiment, the device also includes an image acquisition apparatus 19.

The image acquisition apparatus preferably provides color images, and/or infrared images.

Infrared images advantageously make it possible to view the teeth with an excellent level of contrast.

Preferably, the image acquisition apparatus is a personal device commonly available on the market, for example a mobile phone, a "connected" camera, a smartwatch, a tablet or a fixed or portable personal computer, including an image acquisition system, such as a webcam or a camera, preferably a digital camera. It preferably weighs less than 3 kg, less than 2 kg, less than 1 kg, less than 500 g, preferably less than 300 g.

The image acquisition apparatus may be integrated within the support 12 or be fastened temporarily, by virtue of fastening means 18 that can be deactivated, to the support 12.

In one preferred embodiment, the image acquisition apparatus includes an app configured to guide the operator, in particular so that he or she adjusts the length of the support 12 appropriately. Preferably, the app also guides the patient so that he or she correctly positions his or her mouth on the retractor 14.

In one embodiment, the support 12 is provided with a window through which light from the surroundings may reach inside the chamber 20 in order to illuminate the teeth.

In one preferred embodiment, the device includes a light source 51 that is oriented toward the retractor opening 24 (FIG. 5a) so as to illuminate the teeth of the patient through the retractor opening 24. The light source 51 may in particular emit white light, monochromatic light, infrared radiation or, preferably, ultraviolet radiation.

The light source 51 may be a flash.

In one embodiment, the light source 51 is configured so as to project, onto the teeth, through the retractor opening 24, a reference frame, preferably a laser grid.

Advantageously, the representation of a reference frame on the images facilitates the determination of the shape of the teeth. A first estimation of the shape of the teeth is thus possible without implementing the method described in PCT/EP2015/074896.

In one embodiment, threading is formed on the lateral wall 30 of the box, preferably on the lateral wall of the female part 12b of the box. The threading is preferably shaped so as to allow the support to be fastened to a camera tripod.

In one embodiment, the device also includes an acquisition cover and a retractor cover, which covers are shaped so as to selectively obturate the acquisition opening and the retractor opening in order to facilitate the storage of the device. Preferably, the retractor cover is shaped so as to selectively obturate the retractor opening after dismounting the retractor.

Preferably, the device also includes a processing module 59, in particular an app of the image acquisition apparatus 19 or software loaded on a computer or a tablet.

In the first main embodiment of the invention, the device includes a mirror 16.

The mirror 16 may be fastened to the inner face of the lateral wall 30.

In particular in this embodiment, the mirror 16 is preferably planar. Alternatively, the mirror 16 may be curved. Advantageously, it may then reflect a reflected image representing a region which is difficult to observe with a planar mirror.

The number and the shape of the mirrors are not limiting. In particular, the mirror may be rectangular, spherical, oval, octagonal or hexagonal in shape.

In the embodiment shown in FIG. 1, mirrors 16 cover the entire inner face of the lateral wall of the chamber 20, at least in the female portion 12b of the support 12 and, preferably, also in the male portion 12a of the support.

In one embodiment, the device includes four mirrors each positioned on one of the four faces of the lateral wall of the support, and in particular of the female portion 12b and, preferably, of the male portion 12a of the support. In one preferred embodiment, each mirror entirely covers the face of the support 12 over which it extends.

The length of a mirror may be greater than 3 cm, greater than 5 cm and/or smaller than 30 cm, smaller than 20 cm, smaller than 15 cm, or smaller than 10 cm. The width of a mirror may be greater than 2 cm, greater than 3 cm and/or smaller than 10 cm or smaller than 8 cm.

In the embodiment shown in FIG. 1, the mirrors are fastened to the support, preferably definitively, for example by means of an adhesive.

The mirror 16, preferably each mirror 16, preferably extends in parallel to the X axis. In the embodiment shown, the mirrors 16 extend perpendicularly to one another, pairwise.

Figure 7A:
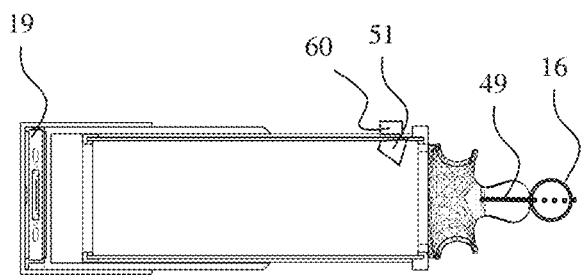
Figure 7B:
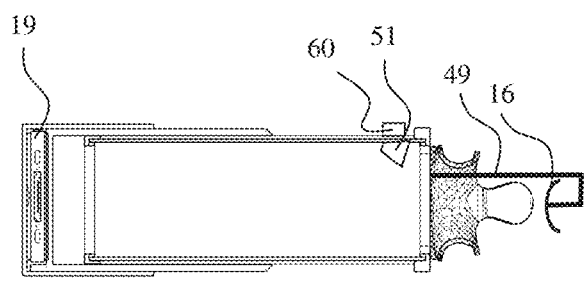

In an embodiment, as represented in FIG. 7a or 7b for instance, the mirror 16 is arranged so as to be placed inside the mouth of the patient in the service position. Therefore, it extends beyond the support, i.e. on the side of the retractor opening which is opposite the support. Advantageously, the mirror can therefore reflect regions of the arcades which are difficult, or even impossible to observe with a mirror exclusively extending outside of the mouth. In particular, it can reflect the inside faces of the teeth.

Preferably, the mirror is extending beyond the retractor, as illustrated in FIG. 7a or 7b, preferably so as to be substantially at the centre of the mouth in the service position.

Preferably, the mirror 16 is curved, for instance in the shape of a sphere (FIG. 7a) or in the shape of a part of a sphere (FIG. 7b), for instance in the shape of a hemisphere, which allows for the reflection of an image representing a large part of the inside faces of the teeth.

The mirror 16 may be fastened, definitely or in a deactivable manner, to the support and/or to the retractor, directly, or indirectly via an arm 49. In an embodiment, the arm is orientable and/or has a variable geometry, i.e. an operator can modify the orientation and/or the shape of the arm. Preferably, the length of the arm can be modified.

Preferably, the orientation of the mirror 16 relative to the arm can be modified. The mirror can in particular be rotatably mounted on the arm or mounted on a ball joint of the arm.

Preferably, as represented in FIG. 7a or 7b, the arm 49 is fixed to the mirror so that it does not obstruct, even partially, the image which is reflected by the mirror 16 towards the image acquisition apparatus. The arm 49 is preferably fixed on a part of the mirror 16 which is not visible on the reflected image.

Using a mirror inside of the mouth advantageously allows for the simultaneous representation, on a same composed image, of the external face, or 'extrados", and of the internal face, or "intrados" of one or several teeth. The simultaneous presence of a mirror and of a light source 51 is particularly advantageous since it makes it possible to acquire images of the teeth that simultaneously show the reflection of the light source 51 off the teeth, but also the reflection of the fictive light source obtained by reflection of the light source 51 by the mirror. Analyzing the relative position of these reflections in the images advantageously makes it possible to roughly determine the orientation of the surface of the teeth returning them, as well as the position of this surface with respect to the acquisition apparatus.

In the second main embodiment of the invention, the device includes a colorimetric calibration chart 52 and/or a translucence calibration chart 54 that is fastened to the support, preferably in the chamber 20.

The number and the shape of the calibration charts are not limiting. In one embodiment of FIG. 6a, the support bears for example three colorimetric calibration charts 52 and three translucence calibration charts 54.

Advantageously, the colorimetric 52 and translucence 54 calibration charts make it possible, for each image, to correct hue errors specific to each image acquisition apparatus.

The colorimetric 52 and translucence 54 calibration charts also advantageously make it possible to determine the exact colors and translucence of the teeth or of the gums, thereby allowing any variation in these properties to be detected.

Preferably, the colorimetric 52 and translucence 54 calibration charts are fastened in proximity to the retractor opening, preferably at less than 5 cm, less than 3 cm, less than 1 cm from the retractor opening. Preferably, the colorimetric 52 and translucence 54 calibration charts are fastened substantially in the plane of the retractor opening, as shown in FIG. 6a.

Preferably, the monitoring module 60 monitors the properties of the radiation emitted by the light source 51, preferably as a function of the luminous radiation received by the retractor opening. A light sensor may be provided, in proximity to the retractor opening, for the purpose of evaluating the luminous radiation received by said retractor opening.

In one embodiment, the monitoring module 60 controls the power of the light source 51 so that more than 50%, more than 70%, more than 90%, or even substantially 100% of the intensity of the radiation received by the retractor opening comes from the light source 51. Implementing a support taking the form of a box that is that is in communication with the outside substantially only via the retractor opening and acquisition opening limits the influence of the outside lighting environment on the box and hence advantageously makes it possible to limit the power of the light source 51.

Such a box also allows more intimate images to be acquired.

Operation

The operation of the device is directly evident from the description above.

The operator first fastens the image acquisition apparatus 19 to the support 12 by means of the fastening means 18, so that the image acquisition apparatus 19 is able to observe both the direct image and the reflected image.

The operator then adjusts the position, along the X axis, of the female portion with respect to the male portion 12a, according to the image acquisition apparatus 19 and its settings. In one embodiment, a scale is arranged on the male portion 12a of the support. Preferably, this scale provides indications facilitating the adjustment of the length, along the X axis, of the support 12, for example by bearing a mark for each type of image acquisition apparatus.

Preferably, the operator switches on the light source 51 so as to illuminate the teeth and to project the reference frame, in particular a laser grid, on the teeth.

The operator also fastens the retractor to the support. In one embodiment shown, he or she inserts a first of the right and left tabs behind a first of the right and left hooks, respectively, then slightly bends the retractor in order to allow the second tab to be inserted behind the second hook. When the operator releases his or her action, the retractor attempts to return to its initial shape, but this return to the initial shape is hindered by the hooks. The pressure of the retractor on the support thus obtained ensures that the retractor is held in position behind the hooks.

Figure 3:
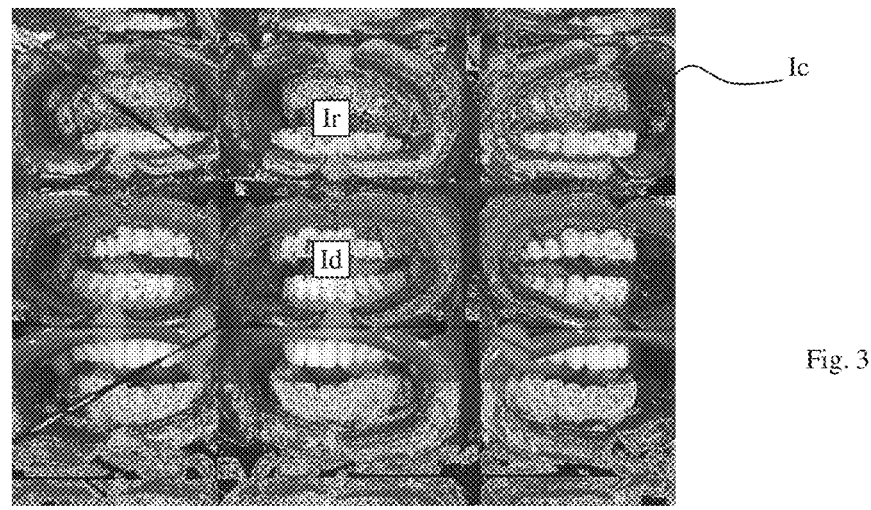
FIG. 3 shows an example of a composite image.
Figure 4A:
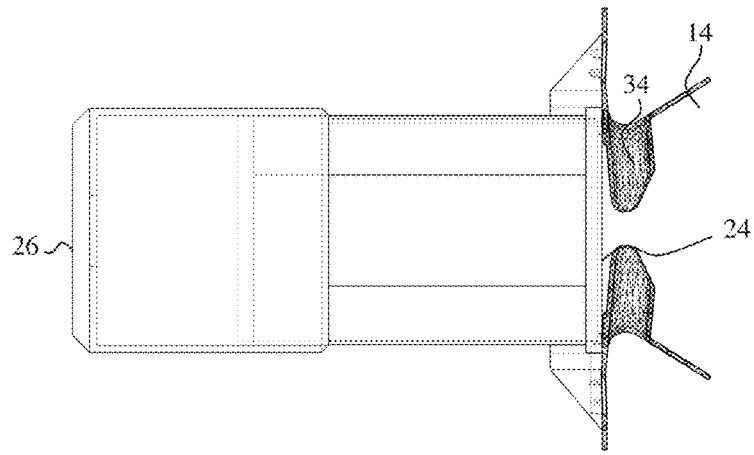
FIGS. 4a, 4b and 4c show the device of FIG. 1 seen from above, seen from the acquisition opening side and seen from the retractor opening side, respectively.
Figure 4B:
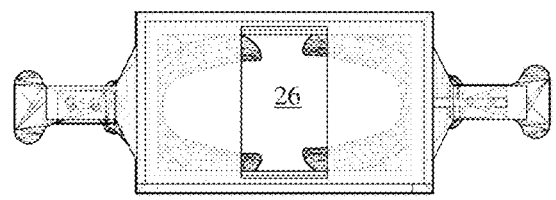
Figure 4C:
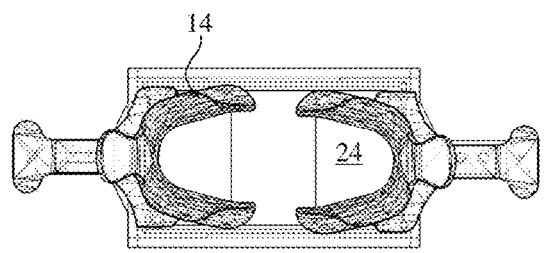

The patient, who may also be the operator, then places his or her lips in the channels defined by the rim 34 of the retractor. As shown in FIG. 3, the teeth of the patient are then clearly visible.

The device is then in a service position in which the image acquisition apparatus 19 views a composite image $I_c$ of the type of that shown in FIG. 3. In this figure, the composite image includes a direct image $I_d$ and eight reflected images $I_r$ reflected by the various mirrors 16 positioned in the chamber 20.

By actuating the trigger of the acquisition apparatus, the operator acquires the composite image $I_c$. Advantageously, he or she simultaneously acquires, like in the embodiment of FIG. 3, a front view (direct image $I_d$) and a set of oblique views (reflected images $I_r$). Of course, the reflected images are inverted with respect to reality. For example, in the reflected image located above the direct image $I_d$, the upper arch is shown below the lower arch.

The reflected images may advantageously correspond to acquisition conditions in which the optical axis of the acquisition apparatus is strongly inclined with respect to the sagittal plane. Using the acquisition apparatus under these conditions, with direct observation, i.e. without a mirror, would often be difficult for the patient.

The composite image is next transmitted to the processing module 59, by wired or wireless means, for example by Wi-Fi or by Bluetooth.

Image processing makes it possible in particular, according to conventional processing methods, to isolate the direct image and the one or more reflected images. In one embodiment, the processing operation also includes an operation of inverting the reflected images and/or an operation of correcting perspective effects, in particular when the mirror is not planar, and/or an operation of correcting colors by means of the colorimetric calibration chart 34.

Analyzing one of the direct and reflected images, preferably the direct image, makes it possible to determine the acquisition conditions of said image, preferably according to the teaching of PCT/EP2015/074896, incorporated by reference. The acquisition conditions of the other images may advantageously be deduced therefrom, simply by taking the geometry of the support 12 into account. In particular, the calibration of the acquisition apparatus is the same for all of the direct and reflected images. Additionally, simple geometric considerations make it possible to determine the position and the orientation of the acquisition apparatus in space which, in the absence of a mirror, would have allowed the acquisition apparatus to acquire a reflected image.

In one embodiment, the processing module 59, preferably integrated within the image acquisition apparatus 19, controls the acquisition of multiple composite images under different acquisition conditions, and in particular with different focal lengths. For example, first, second and third composite images may be acquired by successively focusing the acquisition apparatus on the incisors, on the premolars and on the molars. Advantageously, each tooth is thus shown clearly in at least one of the composite images.

In one embodiment, taking multiple successive images under different acquisition conditions is the result of a single actuation of the trigger of the image acquisition apparatus. In particular, the image acquisition apparatus may be configured to take multiple photographs in succession, with different focal lengths, as a result of a single trigger action.

Furthermore, the acquisition apparatus preferably acquires an image of the teeth of the patient also showing the translucence and colorimetric calibration charts.

The processing module 59, for example an app of the acquisition apparatus, having knowledge of the real color and translucence properties of the calibration charts, then corrects the image until the representations of said calibration charts in the image have these properties.

In order to make the correction accurate, the light source 51 is preferably adjusted so that, at the time of acquisition of the image, the calibration charts are illuminated under the same conditions as when measuring the real properties.

All of the images acquired by the acquisition apparatus are thus advantageously comparable, regardless of the lighting environment outside the device at the moment of their acquisition.

As is now clearly apparent, a device according to the first main aspect of the invention advantageously makes it possible to acquire multiple images very quickly, typically in less than a minute, without recourse to a specialist, in particular to a dentist or an orthodontist. The images may in particular be acquired by the patient him- or herself or by one of his or her kin, using a simple mobile phone, anywhere, and in particular outside of any medical, dental or orthodontics practice.

In addition, if the geometry of the support, and in particular the orientation and the positioning of a mirror, is known, it is enough to determine the acquisition conditions of the direct image in order to be able to determine, by way of simple calculation, the acquisition conditions of the image reflected by this mirror. The implementation of the method described in PCT/EP2015/074896 is considerably accelerated as a result.

Lastly, since the acquisition apparatus 19 is immobile with respect to the teeth, the composite image is advantageously clear and, if the device includes a controlled light source, exhibits good contrast.

The device according to the second main aspect of the invention makes it possible to track variation in the properties of the appearance of the teeth. It also makes it possible for the patient him- or herself to accurately measure these properties at any time, and in particular shortly before a prosthesis is produced, for example. The appearance of the prosthesis is thus particularly close to that of the teeth of the patient.

Of course, the invention is not restricted to the embodiments described and shown, which are provided for illustrative purposes only.

In particular, the mirror is not necessarily planar. It may in particular be configured to compensate for perspective effects and/or to reflect particular regions of the mouth.

The mirror may be movable with respect to the support, and in particular may be translatably movable, in particular to make it possible to modify the distance between the mirror and the retractor opening and/or the acquisition opening.

The mirror may also be rotatably movable, in particular about an axis of rotation that is perpendicular to the X axis of the retractor, two axes being referred to as perpendicular when two planes that are orthogonal to these axes are perpendicular to one another.

Preferably, the image acquisition apparatus includes an app configured to guide the operator so that he or she correctly positions and orients the mirror. In one embodiment, the positioning and/or the orientation of the mirror are facilitated by a scale bearing indications relating to various acquisition apparatuses. The operator may thus easily position the mirror according to the acquisition apparatus used.

In one embodiment, the device includes one or more actuators that are suitable for adjusting the length of the support and/or the positioning and/or the orientation of the mirror according to setpoints, preferably according to setpoints received from the image acquisition apparatus 19.

In one embodiment, the device also includes one or more sensors configured to measure the length of the support 12 and/or the positioning and/or the orientation of the mirror, and a transmitter capable of transmitting said measurement to the image acquisition apparatus.

Advantageously, the device may be optimally configured by controlling the actuators according to a setpoint, preferably provided by the image acquisition apparatus, said setpoint preferably being based on the image observed by the image acquisition apparatus and/or by the measurements taken by the sensors.

Lastly, the number of mirrors is not limited and multiple mirrors, preferably all of the mirrors, preferably have one or more of the preferred features of the mirror 16 described above. In particular, one or more of the mirrors may be provided with a sensor, with an actuator and with means for communicating with the image acquisition apparatus, as described above.

The invention claimed is:

1. An imaging kit including:
   a dental imaging device; and
   an imaging acquisition apparatus;

said dental imaging device including:
a support;
a dental retractor fastened to the support and defining a retractor opening;
at least one mirror fastened to at least one of the support and the retractor; and
means for fastening the image acquisition apparatus to the support in a position in which the acquisition apparatus is oriented so as to receive a composite image including a direct image of the retractor opening and an image of the retractor opening reflected by said at least one mirror;
said image acquisition apparatus being fastened to the device so as to acquire a said composite image,
said dental retractor including a rim extending around the retractor opening and arranged in such way that the patient's lips may rest on it, leaving the patient's teeth visible through said retractor opening.

2. The imaging kit as claimed in claim 1, in which the support defines a chamber that is in communication with the outside via the retractor opening and via an acquisition opening through which the acquisition apparatus fastened by said fastening means receives said composite image.

3. The imaging kit as claimed in claim 2, in which the support is telescopic so that the distance between the retractor opening and acquisition opening is variable.

4. The imaging kit as claimed in claim 1, the device including at least two of said at least one mirror that are oriented perpendicularly to one another and each returning a reflected image of the retractor opening, each of said reflected images being represented in said composite image.

5. The imaging kit as claimed in claim 1, in which the fastening means are chosen from the group consisting of a clip fastener, a self-gripping strip, clamping jaws, a screw, a magnet, a cover and a complimentary shape between the support and the image acquisition apparatus.

6. The imaging kit as claimed in claim 1, in which the fastening means can be deactivated.

7. The imaging kit as claimed in claim 1, the device including a light source that is oriented so as to illuminate the teeth of the patient through the retractor opening.

8. The imaging kit as claimed in claim 7, in which the light source is configured so as to project a reference frame toward the retractor opening.

9. The imaging kit as claimed in claim 1, in which said at least one mirror is fastened so as to extend at least partially inside the mouth of the patient in a service position in which the retractor is on the mouth of the patient.

10. The imaging kit as claimed in claim 1, in which said at least one mirror is curved.

11. The imaging kit as claimed in claim 1, in which said at least one mirror is fastened to the at least one of the support and the retractor via an arm having at least one of a variable geometry, in which the orientation of said at least one mirror relative to the support and the retractor can be modified.

12. The imaging kit as claimed in claim 1, in which the image of the retractor opening which is reflected by said at least one mirror represents the retractor opening as viewed from the inside of the mouth.

13. The imaging kit as claimed in claim 1, in which the acquisition apparatus is a mobile phone.

14. The imaging kit as claimed in claim 1, in which the image acquisition apparatus includes a computer program, and in particular a specialized mobile phone app, comprising program code instructions for at least one of
guiding an operator during at least one of an adjustment to the geometry of the support, when positioning said at least one mirror, when orienting said at least one mirror and when positioning the mouth of the patient on the retractor, and
controlling one or more actuators that are capable of modifying at least one of said geometry, said positioning of said at least one mirror and said orientation of said at least one mirror.

15. The imaging kit as claimed in claim 1, in which the image acquisition apparatus is configured to receive multiple composite images in succession, so as to acquire multiple photographs with different focal lengths, as a result of a single trigger action.

16. The imaging kit as claimed in claim 1, in which the image acquisition apparatus is integrated within the support or is a personal device fastened temporarily to the support.

17. The imaging kit as claimed in claim 1, in which the acquisition apparatus is a "connected" camera, a smartwatch, a tablet or a fixed or portable personal computer, including an image acquisition system.

18. An imaging kit including:
a dental imaging device; and
an imaging acquisition apparatus;
said dental imaging device including:
a support;
a dental retractor fastened to the support and defining a retractor opening;
at least one mirror fastened to at least one of the support and the retractor; and
means for fastening the image acquisition apparatus to the support in a position in which the acquisition apparatus is oriented so as to receive a composite image including a direct image of the retractor opening and an image of the retractor opening reflected by said at least one mirror;
said image acquisition apparatus being fastened to the device so as to acquire a said composite image;
said support taking the form of a box that is in communication with an outside of the box only via the retractor opening and via an acquisition opening.

19. An imaging kit including:
a dental imaging device; and
an imaging acquisition apparatus;
said dental imaging device including:
a support;
a dental retractor fastened to the support and defining a retractor opening;
at least one mirror fastened to at least one of the support and the retractor; and
means for fastening the image acquisition apparatus to the support in a position in which the acquisition apparatus is oriented so as to receive a composite image including a direct image of the retractor opening and an image of the retractor opening reflected by said at least one mirror;
said image acquisition apparatus being fastened to the device so as to acquire a said composite image;
said retractor including lobes arranged to spread cheeks of a patient away from teeth of said patient.

* * * * *